(12) United States Patent
Atis et al.

(10) Patent No.: US 8,586,016 B2
(45) Date of Patent: Nov. 19, 2013

(54) HYDROCARBON COMPLEX MASCARA

(75) Inventors: Balanda Atis, Newark, NJ (US); Florentina Pavel, Perth Amboy, NJ (US)

(73) Assignee: L'Oreal (FR)

( * ) Notice: Subject to any disclaimer, the term of this patent is extended or adjusted under 35 U.S.C. 154(b) by 1258 days.

(21) Appl. No.: 11/374,486

(22) Filed: Mar. 13, 2006

(65) Prior Publication Data

US 2007/0212317 A1 Sep. 13, 2007

(51) Int. Cl.
*A61K 8/90* (2006.01)
*A61K 8/31* (2006.01)

(52) U.S. Cl.
USPC ........................... 424/70.7; 424/70.11

(58) Field of Classification Search
USPC ............................ 424/70.7, 70.11
See application file for complete search history.

(56) References Cited

U.S. PATENT DOCUMENTS

| | | | |
|---|---|---|---|
| 5,294,438 A | 3/1994 | Chang et al. | |
| 5,874,072 A | 2/1999 | Alwattari et al. | |
| 5,972,324 A * | 10/1999 | Zofchak et al. | 424/78.03 |
| 6,083,516 A | 7/2000 | Curtis et al. | |
| 6,248,336 B1 | 6/2001 | McDermott | |
| 6,303,105 B1 * | 10/2001 | Shah et al. | 424/61 |
| 6,403,070 B1 | 6/2002 | Pataut et al. | |
| 6,423,306 B2 * | 7/2002 | Caes et al. | 424/78.02 |
| 6,503,521 B1 | 1/2003 | Atis et al. | |
| 6,517,823 B1 | 2/2003 | Norman et al. | |
| 6,534,047 B1 | 3/2003 | Bodelin | |
| 6,641,821 B1 * | 11/2003 | Collin et al. | 424/401 |
| 6,716,419 B2 * | 4/2004 | Zoltowski et al. | 424/64 |
| 6,726,917 B2 | 4/2004 | Kanji et al. | |
| 7,884,158 B2 * | 2/2011 | Bui et al. | 525/64 |
| 2002/0031488 A1 | 3/2002 | Kanji et al. | |
| 2003/0185782 A1 | 10/2003 | Auguste et al. | |
| 2004/0009198 A1 | 1/2004 | Bernard et al. | |
| 2004/0047884 A1 | 3/2004 | Bernard et al. | |
| 2004/0052745 A1 | 3/2004 | Bernard et al. | |
| 2005/0106193 A1 | 5/2005 | Zofchak et al. | |
| 2005/0180936 A1 | 8/2005 | Pays | |
| 2005/0197479 A1 | 9/2005 | Pavlin | |
| 2006/0013839 A1 * | 1/2006 | Yu | 424/401 |

FOREIGN PATENT DOCUMENTS

| | | |
|---|---|---|
| FR | 2840204 A1 | 12/2003 |
| JP | 2001503071 A | 3/2001 |
| JP | 2001518929 A | 10/2001 |
| JP | 2002537314 A | 11/2002 |
| JP | 2005225867 A | 8/2005 |
| JP | 2005247730 A | 9/2005 |
| JP | 2005528471 A | 9/2005 |
| JP | 2006502155 A | 1/2006 |
| WO | 98/42298 A1 | 10/1998 |
| WO | 99/22711 A1 | 5/1999 |
| WO | 00/49997 A1 | 8/2000 |
| WO | 0215875 A2 | 2/2002 |
| WO | 2007/015166 | 2/2007 |
| WO | 2007/031872 | 3/2007 |

OTHER PUBLICATIONS

Nagura, T. et al., "Oily Cosmetics for Eyelashes", JP 2005-247730, Sep. 15, 2005, machine translation.*
Exxon Mobil Chemical—Synthesis, Summary of Safety Data on PureSynÔ Polyalphaolefins (May 2004).
Extended European Search Report for Application No. EP07251014 dated Jul. 22, 2013.

* cited by examiner

*Primary Examiner* — Gina C Justice
(74) *Attorney, Agent, or Firm* — Lerner, David, Littenberg, Krumholz & Mentlik, LLP

(57) ABSTRACT

Disclosed are mascara compositions that contain a thermoplastic elastomer, a tackifier, a volatile solvent, and a nonpolar non-volatile solvent, and methods of making and using the compositions.

24 Claims, No Drawings

US 8,586,016 B2

HYDROCARBON COMPLEX MASCARA

BACKGROUND OF THE INVENTION

The cosmetic industry focuses much of its efforts, in regards to mascara, on increasing two fundamental properties, namely enhancing volume or thickness of eyelashes and extending length of wear. U.S. Pat. No. 5,874,072 teaches mascara containing a mixture of water-insoluble copolymers in the form of an aqueous emulsion with water-soluble film-forming polymers. U.S. Pat. No. 6,248,336 teaches mascara compositions with improved wear characteristics in the form of an emulsion comprising an insoluble polymeric material in an aqueous emulsion, and lipophilic oil components including a polyvinylpyrrolidone/hexadecane copolymer. U.S. Pat. No. 6,534,047 teaches cosmetic compositions for coating keratin fibers, containing a cationic polymer, an anionic polymer and an aqueous dispersion of a $C_1$-$C_6$ alkyl (meth)acrylate. The patents teach that the compositions lead rapidly to a uniform make-up result that have good properties of coating, lengthening and curling the eyelashes, as well as good staying power.

U.S. Pat. No. 6,503,521 teaches mascara that enhances volume via the use of three film formers, namely: at least one tacky film former soluble or dispersible in water; at least one tacky film former soluble in oil; and at least one additional water-soluble or water-dispersible film former. U.S. Pat. No. 6,726,917 teaches mascara for providing volume and/or length to eyelashes, containing fibers, pigments, and at least two film formers: at least one tacky film former soluble or dispersible in water; and at least one tacky film former soluble in oil chosen from hydrogenated polyisobutenes, adipic acid/diethylene glycol/glycerin crosspolymers, polyethylenes, and polyvinyl laurates.

SUMMARY OF THE INVENTION

A first aspect of the present invention is directed to mascara containing a thermoplastic elastomer, a tackifier, a volatile solvent, and a non-polar non-volatile solvent. In some embodiments, the mascara also contains water and an emulsifier, which in some embodiments results in a mascara that is washable. The emulsifier preferably does not contain triethanolamine. Methods of making the mascara by mixing together the aforementioned ingredients, and methods of applying mascara to eyelashes, or to increasing volume of eyelashes, are also disclosed.

Applicants have unexpectedly discovered that mascara compositions of the present invention not only provide greater volume and length, but also increased wear and color intensity, particularly in embodiments where the mascara is waterproof. They have also discovered that fiber formation which occurs when the applicator is drawn away from the eyelashes after application of the mascara, (and is analogous to the fiber-like strings of hot cheese between the pizza slice and the pie when the slice is taken away from the pie) is reduced, particularly compared to mascara that does not contain the non-volatile solvent.

DETAILED DESCRIPTION OF THE INVENTION

Mascara may be formulated as washable or waterproof. The term washable mascara, as used herein, refers to compositions that may be removed with water and/or soap. These formulations are typically emulsions (e.g., of waxes in water) such as creams, or in some cases gels and cakes. Waterproof mascara, which requires use of oils for removal, generally comes in the form of dispersions of waxes in organic solvents.

The mascara of the present invention, waterproof and washable alike, contain a thermoplastic elastomer having a thermoplastic segment comprising styrene, a tackifier, a volatile solvent, and a non-volatile solvent.

Thermoplastic elastomers have at least two thermodynamically incompatible segments, namely a "thermoplastic" or "hard" segment, and an "elastomeric" or "soft" segment. Aside from their compositional nature, hard and soft segments differ in terms of their glass transition temperatures, "Tg". More particularly, the hard segment has a Tg of at least about 50° C., whereas the soft segment has a Tg of about −10° C. or below. See, e.g., U.S. Pat. Nos. 5,294,438 and 6,403,070.

The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like. In preferred embodiments, the hard or thermoplastic segment of the elastomer contains (or in some embodiments, consists of) styrene. In some embodiments wherein the mascara is waterproof, the styrene content of the thermoplastic elastomer is less than 30% by weight, or less than 25% by weight, or even less than 20% by weight, based on the weight of the thermoplastic elastomer (i.e., solids content). This is because of the tendency of thermoplastic elastomers having a styrene content of greater than 30% by weight to harden/gel in conventional carrier systems. However, in the event that a thermoplastic elastomer having a styrene content of greater than 30% by weight is used, it will be necessary to also employ a solvent or functional ingredient capable of dissolving a styrene block in an amount effective to control the hardening/gelling of the styrene-containing elastomer in the cosmetic composition. In yet other embodiments, the styrene content is less than about 13% by weight.

The soft segments of the thermoplastic elastomer comprise olefin polymers and/or copolymers which may be saturated, unsaturated, or combinations thereof. Examples of suitable olefin copolymers include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In some embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains contain a di-block, tri-block, multi-block or radial or star block configuration or numerous mixtures thereof. The Kraton™ tri-block rubbers have polystyrene (hard) segments on each end of a rubber (soft) segment, while the Kraton™ diblock rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to contain block segments of styrene monomer units and rubber monomer and/or co-monomer units. The most common structure for the Kraton™ triblock copolymer is the linear A-B-A block type styrene-butadienestyrene, styrene-isoprene-styrene, styrene-ethylenepropylene-styrene, or styrene-ethylenebutylene-styrene. The Kraton™ di-block is typically the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g., hydrogenated styrene-butylene/ethylene-styrene copolymer (tri-block)).

The thermoplastic elastomers according to the invention may be chosen from adhesives of "pressure-sensitive adhesive" type for example, such as those mentioned in the "Handbook of Pressure Sensitive Adhesive Technology" 3rd Edition, D. Satas. The thermoplastic elastomers according to the invention may also be adhesive polymers chosen from polyurethanes, ethylene/vinyl acetate polymers, and blends thereof.

The thermoplastic elastomers of the present invention are typically employed in gelled form. By the term "gelled," it is meant that the block copolymer is dissolved in a solvent. The block copolymer is formulated by dissolving it in a solvent such as oils, hydrocarbon solvents and esters. Hydrocarbons useful in the practice of the invention include but are not limited to mineral oils, mineral solvents, mineral spirits, petroleum, waxes, synthetic hydrocarbons, animal oils, vegetable oils, and mixtures thereof. In some embodiments, the block copolymer is formulated by dissolving the block copolymer in isododecane or a light paraffinic solvent. Specific examples of thermoplastic elastomers in gelled form include, but are not limited to, Versagel™ M5960 and Versagel™ M5970, commercially available from Penreco of Houston Tex., as well as those from Brooks Industries, such as Gel Base (e.g., Code 05895, which is a styrene-ethylene/propylene mixed block copolymer already in combination with a solvent, namely isododecane).

The thermoplastic elastomer may be formed by dissolving a block copolymer in a non-hydrocarbon solvent such as amyl acetate, butyl acetate, isobutyl acetate, ethyl acetate, propyl acetate or isopropyl acetate. The solvent and solubility conditions for formulating a block copolymer film former from a block copolymer will be chosen by a person skilled in the art in order to prepare a composition which has the desired properties. One of ordinary skill in the art will be able to determine the solubility parameters and choose a solvent based on the block copolymer chosen for the envisaged application. More information regarding solubility parameters and solvents useful in the processing of specific block copolymers is available from the various manufacturers of block copolymers, e.g., Shell Chemical Company. Additional discussions of polymer solubility parameter concepts are presented in: *Encyclopedia of Polymer Science and Technology*, Vol. 3, Interscience, New York (1965) and *Encyclopedia of Chemical Technology*, Supp. Vol., Interscience, New York (1971).

In some embodiments, the thermoplastic elastomer is a tri-block rubber elastomer. The tri-block rubber elastomer can be styrene ethylene/butylene tri-block copolymers. Representative examples of styrene ethylene/butylene tri-block copolymers are Kraton™ G polymers, e.g., Kraton™ G1657M, commercially available from Shell.

The amount of the thermoplastic elastomer in the mascara generally ranges from about 0.1% to about 40%, and in some embodiments from about 0.5% to about 10%, expressed as percent solids, and by weight of the mascara.

A substance is described as a tackifier if, by adding it to the thermoplastic elastomer, the resulting composition has the properties of a pressure sensitive adhesive. In general, tackifiers can be divided into four different families in terms of their chemistry, namely hydrocarbon resins, terpenes, amorphous (i.e., non-crystalline) rosins, and rosin esters and their derivatives. These tackifiers are characterized by their compatibility with at least one segment of the thermoplastic elastomer. By the term "compatible", it is meant that when the thermoplastic elastomer and tackifier are mixed, the combination of at least one segment of the thermoplastic elastomer with the tackifier forms a polymer blend having a single glass transition temperature Tg which may be measured by DMA, DSC or neutron light scattering.

The compatibility of the thermoplastic elastomer and the tackifier may also be defined in terms of solubility parameters. The solubility parameter $\delta$ according to the Hansen solubility space is defined in the article "Solubility Parameter Values" by Eric A. Grulke in "*Polymer Handbook,*" 3rd edition, Chapter VII, pages 519-559, by the relationship:

$\delta = (dD2 + dP2 + dH2)^{1/2}$, in which dD characterizes the London dispersion forces resulting from the formation of dipoles induced during molecular impacts; dP characterizes the forces of Debye interactions between permanent dipoles; and dH characterizes the forces of specific interactions (hydrogen bond, acid/base or donor/acceptor type and the like). The definition of the solvents in the three-dimensional solubility space according to Hansen is given in C. M. Hansen: "*The three-dimensional solubility parameters,*" in J. Paint Technol., 39, 105(1967).

The tackifier used in the present invention will have a solubility parameter corresponding to $\delta$ and the thermoplastic elastomer will have at least one segment whose solubility parameter corresponds to $\delta \pm 2$, and in some embodiments $\delta \pm 1.7$, $\delta \pm 1.5$, $\delta \pm 1.3$, $\delta \pm 1.0$, $\delta \pm 0.7$, $\delta \pm 0.5$, or $\delta \pm 0.3$.

Examples of suitable tackifiers include aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, and hydrogenated rosin esters. The tackifier may be fully or partially hydrogenated. The tackifier may also be non-polar. As used herein, non-polar refers to a tackifier that is substantially free of monomers having polar groups. In some embodiments, the polar groups are not present; however, if they are present, they are typically present in an amount of up to about 5% by weight, and in some embodiments, up to about 2% by weight, or up to about 0.5% by weight. In some embodiments, the tackifier may have a softening point (Ring and Ball ("R and B"), as measured by ASTM E-28) of 80° C. to 150° C., preferably 100° C. to 130° C. In other embodiments, the tackifier may be liquid and have an R and B softening point of between about −70° C. and 70° C.

In some embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the tradename Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

The tackifier is present in the cosmetic composition of the present invention in an amount of from about 0.1% to about 70% by weight, and in some embodiments from about 0.5% to about 40% by weight, based on the weight of the composition.

Representative volatile solvents include non-polar volatile hydrocarbon-based oils (which as used herein, refers to oil containing only hydrogen and carbon atoms), silicone oils (optionally comprising alkyl or alkoxy groups that are pendant or at the end of a silicone chain), and fluoro oils. Suitable hydrocarbon-based oils include isoparaffins, i.e., branched alkanes containing 8-16 carbon atoms, such as isododecane (also known as 2,2,4,4,6-pentamethylheptane), and petroleum distillates. Suitable silicone oils may include linear or cyclic silicones containing from 2 to 7 silicon atoms, these silicones optionally comprising alkyl or alkoxy groups containing from 1 to 10 carbon atoms. Mention may thus be made especially of octamethylcyclotetrasiloxane, decamethylcyclopentasiloxane, hexadecamethylcyclohexasiloxane, heptamethylhexyltrisiloxane and heptamethyloctyltrisiloxane, and mixtures thereof. Mixtures of these solvents may be used. Polar volatile solvents may also be used, examples of which include C2 to C5 alcohols, such as ethanol, ethyl 3-ethoxypropionate and isohexyl neopentanoate. The volatile solvent is present in the mascara of the present invention in an amount generally ranging up to about 90%, and in some embodiments, about 5% to about 80%, and in other embodiments, from about 10% to about 70%, based on the total weight of the mascara.

Exemplary non-polar non-volatile solvents include polyalphaolefins, which include ethylene derivatives oligomerized into even-numbered carbon polyalphaolefins e.g., C6-C14 olefins such as polydecene and polymers of C6, C8, C12 and C14 olefins. The polyolefins may have a molecular weight (MW) generally ranging from about 280 to about 11,500, and a viscosity (CPs at 20° C.) generally ranging from about 7 to about 32,500. They may also be hydrogenated. In some embodiments, the non-volatile solvent includes PureSyn™ 2 (MW about 283), 4 (MW about 432), 6 (MW about 570), 8 (MW about 611), 150 (MW about 3980) and 300 (MW about 4870) (INCI name: hydrogenated polydecene). The viscosity of these polymers is about 8, about 33, about 64, about 103, about 4179 and about 8400, respectively.) PureSyn™ 100 (MW about 2939, viscosity about 3900, INCI name:hydrogenated C6-14 olefin polymers) and PureSyn™ 1000 (MW about 11,500, viscosity about 32,400, INCI name: polydecene) may also be useful. The PureSyn™ products are available from Exxon Chemicals.

The non-volatile solvent is present in the mascara of the present invention in an amount generally ranging from about 0.1% to about 70%, and in some embodiments, about 0.5% to about 40%, and in other embodiments, 1% to about 25%, based on the total weight of the mascara.

The inventive compositions may contain any other cosmetically or dermatologically acceptable and, in general, physiologically acceptable oil, such as carbon-based, hydrocarbon-based, fluoro and/or silicone oils, of mineral, animal, plant or synthetic origin, alone or as a mixture. These ingredients, along with the non-polar solvents, would constitute a liquid fatty phase of the mascara composition.

Washable mascara of the present invention also contains water, which may or may not be present in waterproof mascara. Generally, water content of washable mascaras ranges from about 20 to about 80% by weight, and in some embodiments from about 30 to about 60% by weight of the mascara composition. In contrast, water content of waterproof mascaras generally ranges from about 0 to about 60% by weight, and in some embodiments from about 0 to about 35% by weight of the mascara composition. One or more water-miscible solvents may also be present.

In addition to water, the aqueous phase may contain a water-miscible solvent (miscibility in water of greater than 50% by weight at 25° C.), for instance, lower monoalcohols containing from 1 to 5 carbon atoms such as ethanol or isopropanol, glycols containing from 2 to 8 carbon atoms, such as propylene glycol, ethylene glycol, butylene glycol or dipropylene glycol and pentylene glycol, C3-C4 ketones and C2-C4 aldehydes.

The compositions of the invention may contain an emulsifier. Emulsifiers typically employed in the compositions of the present invention include anionic, nonionic and cationic emulsifiers. See, e.g., *Encyclopedia of Chemical Technology, KIRK-OTHMER*, volume 22, pp. 333-432, 3rd edition, 1979, Wiley, for the definition of the properties and (emulsifying) functions of the emulsifiers, in particular pp. 347-377 of this publication regarding anionic and nonionic emulsifiers. Examples of emulsifiers useful in the compositions of the invention are include as nonionic emulsifiers, fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated $C_1$-$C_6$ alkyl glucose fatty esters, and as anionic emulsifiers, $C_{16}$-$C_{30}$ fatty acids neutralized by amines, ammonia or the alkali metal salts thereof. Examples of cationic emulsifiers include quaternary amines, amine oxides and amines, e.g., alkyl amines, alkyl imidazolines, ethoxylated amines, quaternary compounds, and quaternized esters. Cationic emulsifiers may also provide a conditioning effect.

In some embodiments, the emulsifier excludes triethanolamine (TEA) or a TEA-containing compound such as TEA-stearate and TEA-glyceryl stearate. In these embodiments, the emulsifier is phosphate-based emulsifier, examples of which include monoalkyl phosphates (MAP) and dialkyl phosphates, such as the lauryl monophosphate sold under the name MAP 20® by the company Kao Chemicals, the potassium salt of dodecylphosphoric acid, as a mixture of monoester and diester (mainly diester), sold under the name Crafol AP-31® by the company Cognis, the mixture of monoester and diester of octylphosphoric acid, sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium salt or triethanolamine salt of monoalkyl (C12-C13) phosphate sold under the references Arlatone MAP 230K-40® and Arlatone MAP 230T-60® by the company Uniqema, and the potassium lauryl phosphate sold under the name Dermalcare MAP XC-99/09® by the company Rhodia Chimie. In some embodiments, the phosphate emulsifier is Arlatone MAP 160K® (INCI name: potassium cetyl phosphate), available from Uniquema.

Emulsifiers are generally present in amounts ranging from about 1 to about 30% by weight, and in some other embodiments from about 3% to about 15% by weight, relative to the total weight of the composition.

The compositions of the present invention may further contain at least one suitable (e.g., cosmetically or dermatologically acceptable) ingredient, including additives and adjuvants, including, for example, waxes, polymers, thickeners, moisturizers, colorants, dispersion enhancing agents, fillers (e.g., powders and Mothers of pearl), fibers, sunscreen agents, preservatives, chelators (such as EDTA and salts thereof, particularly sodium and potassium salts), antioxidants (e.g., BHT, tocopherol), essential oils, fragrances, neutralizing or pH-adjusting agents (e.g., sodium hydroxide), and cosmetically active agents and dermatological active agents such as, for example, anti-inflammatory agents, defoaming agents, emollients, vitamins, trace elements and essential fatty acids. These ingredients may be soluble or dispersible in the aqueous or the fatty phase.

For the purposes of the present invention, the term "wax" means a lipophilic fatty compound that is solid at room temperature (25° C.) and atmospheric pressure (760 mmHg, i.e., $10^5$ Pa), which undergoes a reversible solid/liquid change of state and which has a melting point of greater than 30° C. and in some embodiments, greater than 55° C. up to 120° C. or even as high as 200° C.

For the purposes of the invention, the waxes are those generally used in cosmetics and dermatology. A variety of waxes may be useful, including waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candellila wax, ouricurry wax, cork fibre waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes. Alternatively, hydrogenated oils of animal or plant origin may be used. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils. In some embodiments, the compositions contain at least two or at least three waxes. The wax may be present in the compositions in an amount generally ranging from about 0.1% to about 40%, and in some embodiments from about 0.5% to about 20%, or from about 1% to about 10% by weight, relative to the total weight of the composition.

The mascara compositions may contain other polymers, e.g., film forming polymers that are compatible with the other ingredients and form a film after application. Suitable polymers include polyvinylpyrrolidones (PVP) and vinyl copolymers, e.g., vinyl pyrrolidone (VP)/hexadecane copolymer, PVP/hexadecene copolymer and VP/eicosene copolymer (e.g., Ganex V220, which is a trade name of ISP Inc. of Wayne, N.J.), trimethylsiloxysilicate and acrylates copolymer. The polymer may be present in the compositions in an amount generally ranging from 0 to about 20% by weight.

Viscosity may be adjusted by adding an oil phase thickener or an agent useful for gelling a liquid fatty phase. Gelling agents may be chosen from gelling agents in polymeric form and gelling agents in mineral form. The gelling agent may be selected from the group consisting of agents that gel via chemical reticulation and agents that gel via physical reticulation. Modified clays may be used as gelling agents, examples of which include hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox. Other mineral gelling agents include silica, such as fumed silica. The fumed silica may have a particle size ranging from about 5 nm to 200 nm.

Water-soluble thickeners or gelling agents that may be used include polyvinylpyrrolidone (PVP), polyvinyl alcohol, crosslinked acrylates (e.g. Carbopol 982), hydrophobically-modified acrylates (e.g. Carbopol 1382); polyacrylamides such as, for example, the crosslinked copolymers sold under the names Sepigel 305 (CTFA name: polyacrylamide/C13-C14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulphonic acid polymers and copolymers, that are optionally crosslinked and/or neutralized; cellulose derivatives such as hydroxyethylcellulose, sodium carboxymethylcellulose, hydroxypropyl methylcellulose, hydroxypropyl cellulose, ethyl cellulose and hydroxymethyl cellulose; polysaccharides and gums, e.g., natural gums such as xanthan gum, sclerotium, carrageenan and pectin; polysaccharide resins such as starch and its derivatives, hyaluronic acid and its salts, clays, and, in particular, montmorillonites, hectorites, bentonites, and laponites, crosslinked polyacrylic acids, such as the "Carbopol" products from the company Goodrich, the polyglyceryl (meth)acrylate polymers sold under the names "Hispagel" or "Lubragel" by the companies Hispano Quimica or Guardian, crosslinked acrylamide polymers and copolymers, such as those sold under the names "PAS 5161" or "Bozepol C" by the company Hoechst, "Sepigel 305" by the company SEPPIC, crosslinked methacryloyloxyethyltrimethylammonium chloride homopolymers sold under the name "Salcare SC95" by the company Allied Colloid, and associative polymers and, in particular associative polyurethanes.

In some embodiments, the compositions contain a thickener which is a fatty alkoxylated dimeric compound. Suitable fatty alkoxylated dimeric compounds include those disclosed in U.S. patent application publication No. U.S. 2005/0106193, published May 19, 2005. More specifically, suitable fatty alkoxylated dimeric compounds include compounds of the formula (I):

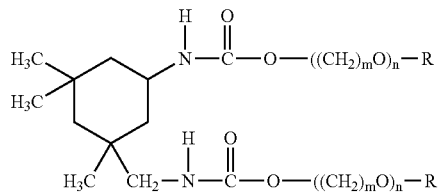

where n is a whole number between about 50 and about 150, preferably between about 70 and about 120, and most preferably between about 75 and about 100, including all ranges and subranges therebetween; m is a whole number between 1 and 5, preferably 2 and/or 3 (ethoxylation and/or propoxylation), and most preferably 2 (ethoxylation); and R represents a $C_{12}$-$C_{24}$ alkyl or alkenyl fatty portion, preferably a $C_{14}$-$C_{22}$ fatty portion, and most preferably a a $C_{16}$-$C_{18}$ fatty portion. Preferred fatty alkoxylated dimeric compounds are compounds comprising between about 75 and about 100 ethoxylated units and a $C_{16}$-$C_{18}$ fatty portion. Particularly preferred examples of such compounds are compounds having 75 or 100 mole (or units) of ethoxylation marketed under the tradenames Dermothix 75 and Dermothix 100, respectively.

The thickening/gelling agent is generally present in an amount ranging from about 0.05% to about 20% by weight, and in some embodiments from about 0.5% to about 10% by weight.

Compositions of the present invention may also contain a moisturizer. Examples include sodium lactate, mannitol, amino acids, hyaluronic acid, lanolin, urea, petroleum jelly and mixtures thereof. Other examples include polyols such as glycerin, diglycerin, triglycerin, polyglycerin, polyethylene glycol, ethylene glycol, diethylene glycol, triethylene glycol, propylene glycol, dipropylene glycol, hexylene glycol, 1,3-butylene glycol, 1,4-butylene glycol and sorbitol. These agents are present in the compositions of the present invention in amounts generally ranging from about 0.1% to about 20%, and in some embodiments, from about 0.5% to about 15% by weight of the composition.

Colorants may be chosen from the lipophilic dyes, hydrophilic dyes, traditional pigments, and nacres usually used in cosmetic or dermatological compositions, and mixtures thereof. The coloring agent may have any shape, such as, for example, spheroidal, oval, platelet, irregular, and mixtures thereof. Pigments may optionally be surface-treated e.g., with silicones (e.g., inorganic pigments may be coated with simethicone), perfluorinated compounds, lecithin, and amino acids.

The liposoluble dyes include, for example, Sudan Red, D&C Red 17, D&C Green 6, soybean oil, Sudan Brown, D&C Yellow 11, D&C Violet 2, D&C Orange 5, quinoline yellow and annatto. The water-soluble dyes are, for example, beetroot juice or methylene blue.

The pigments may be chosen from white pigments, colored pigments, inorganic pigments, organic pigments, coated pigments, uncoated pigments, pigments having a micron size and pigments not having a micron size. Among the inorganic pigments that may be mentioned are titanium dioxide, optionally surface-treated, zirconium oxide, zinc oxide, cerium oxide, chromium oxide, manganese violet, ultramarine blue, chromium hydrate, and ferric blue. Among the organic pigments which may be mentioned are carbon black, pigments of D&C type, lakes based on cochineal carmine, lakes based on barium, lakes based on strontium, lakes based on calcium, and lakes based on aluminum.

The nacreous pigments may, for example, be chosen from white nacreous pigments such as mica coated with titanium and mica coated with bismuth oxychloride, colored nacreous pigments such as titanium mica with iron oxides, titanium mica with, for example, ferric blue and/or chromium oxide, titanium mica with an organic pigment of the type mentioned above, as well as nacreous pigments based on bismuth oxychloride, interferential pigments, and goniochromatic pigments.

Colorants are generally be present in an amount ranging from about 0.01% to about 50% relative to the total weight of the composition.

The compositions of the present invention may also contain dispersion enhancing agents such as polysaccharide resins, e.g., KM 13, available from KAMA International Corp. (Duluth, Ga.). Dispersion enhancing agents are especially preferred in pigmented products.

Fillers, powders and mothers-of-pearl may also be added to the formulations, typically to modify the texture of the composition and the matteness/gloss effect. Fillers should be understood to mean lamellar or non-lamellar, inorganic or synthetic, colorless or white particles. Mothers-of-pearl should be understood to mean iridescent particles produced especially by certain mollusks in their shell or else synthesized. Representative examples of these ingredients include mica, silica, kaolin, iron oxides, titanium dioxide, polyamide powders, polyamide powders, for instance Nylon® (Orgasol from Atochem), poly-alanine powders, polyethylene powders, tetrafluoroethylene polymer powders, for instance Teflon®, starch, boron nitride, hollow polymer microspheres such as those of polyvinylidene chloride/acrylonitrile, for instance Expancel® (Nobel Industrie), acrylic powders such as Polytrap® (Dow Corning), polymethyl methacrylate particles and silicone resin microbeads (for example Tospearls® from Toshiba), magnesium hydrocarbonate, hydroxyapatite, hollow silica microspheres (Silica Beads® from Maprecos), and glass and ceramic microcapsules. Filler(s), if present, are in amounts generally ranging from about 0.1% to about 25%, and in some embodiments from about 1% to about 20% by weight of the total weight of the composition.

In some embodiments, the mascara may further contain fibers to allow an improvement in the lengthening effect. The fibers useful in the present invention may be chosen from natural and synthetic fibers. Natural fibers include, but are not limited to, cotton, silk, wool, and other keratin fibers. Synthetic fibers include, but are not limited to, polyester, rayon, nylon and other polyamide fibers. The fibers may be present in the compositions in an amount generally ranging from about 0.01% to about 10% by weight of the composition.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben), and phenoxyethanol. Mixtures of preservatives are also useful, e.g., the mixture of methylparaben, ethylparaben, propylparaben and butylparaben sold under the name Nipastat by Nipa, the mixture of phenoxyethanol, methylparaben, ethylparaben, propylparaben and butylparaben, also sold by Nipa under the name Phenonip, and the mixture of phenoxyethanol, methylparaben, isopropylparaben, isobutylparaben and butylparaben, sold by ISP under the name Liquapar Optima. The preservative may be present in an amount generally ranging from about 0.01% to about 15% by weight of the composition.

The following examples are intended to further illustrate the present invention. They are not intended to limit the invention in any way. Unless otherwise indicated, all parts are by weight.

Example 1

| Waterproof Mascara | |
|---|---|
| MATERIALS | AMOUNT |
| Isododecane | 47.08 |
| Regalite® R 1100 | 21.46 |
| Kraton ™ G 1657 M | 2.65 |
| Bentone | 7.53 |
| Propylene Carbonate | 2.45 |
| PureSyn ™ 2 | 11.30 |
| DC 556 | 7.53 |
| TOTAL | 100.00 |

To make the waterproof mascara, isododecane was heated in the main kettle to a temperature of 65-80° C. Under mixing, Regalite® R 1100 was added and dissolved (about 15 minutes). After the solid was completely dissolved, the Kraton G 1657 M was added under vigorous mixing. The temperature was maintained between 60 and 80° C. After all solids were dissolved, the bentone was added, and once that was dissolved, propylene carbonate was added and mixed well. When the mixture was homogenous, the PureSyn™ 2 and DC 556 were added, and mixed until homogenous. When the temperature reached 30-35° C., the batch was dropped.

Example 2

| | Washable Mascara | |
|---|---|---|
| PHASE | MATERIALS | AMOUNT |
| A | Water | 51.60 |
| | Hydroxypropylcellulose | 0.20 |
| | PVP K90 | 1.00 |
| | Pentylene Glycol | 2.00 |
| | Methylparaben | 0.35 |
| | Disodium EDTA | 0.10 |
| | 50% Sodium Hydroxide Solution | 1.00 |
| B | Beeswax | 4.00 |
| | Paraffin | 3.00 |
| | Carnauba Wax | 4.00 |
| | Propylparaben | 0.05 |
| | Ganex V220 | 4.00 |
| | Black Iron Oxide | 5.50 |
| | Potassium Cetyl Phosphate | 6.00 |
| C | Simethicone | 0.10 |
| D | Regalite ® R1100 | 8.00 |
| | Kraton ™ G1657M | 1.00 |
| | Isododecane | 5.00 |
| E | PureSyn ™ 2 | 2.00 |
| F | Liquapar Optima | 1.10 |
| | TOTAL | 100.00 |

To make the washable mascara, phase B ingredients were combined and melted to 90° C., and upon achieving uniformity, the black iron oxide was added under conditions of homo-mixing for one hour. In a separate beaker, the de-ionized water, pentylene glycol, methylparaben and the disodium EDTA were added. Mixing was begun using a propeller with initiation of heating to 85° C. While mixing, PVP K90 was added, followed by addition of hydroxypropylcellulose while heating to 85° C. To this mixture, the 50% sodium hydroxide was added to the other phase A ingredients. The phase B ingredients were added to the other phase A ingredients, and homogenized for 30 minutes for 80-85° C. Five minutes later, phase C. ingredient (i.e., simethicone) was added. Thirty minutes later, the batch was removed from the homogenizer, and mixed under paddle mixing. Phase D ingredient (i.e., Regalite® R1100) was added at 60° C., followed by addition of the phase E ingredient (i.e., PureSyn™ 2) at 50° C., followed by addition of the phase F ingredient (i.e., Liquapar Optima), at 45° C. The temperature of the resulting formulation was lowered to 30-35° C.

Example 3

| MATERIALS | AMOUNT |
|---|---|
| Isododecane | 56.0 |
| Regalite ® R 1100 | 16.0 |
| Kraton ™ G 1657 M | 2.0 |
| Uniclear 100 VG | 12.0 |
| Disteardimonium Hectorite | 3.0 |
| Black Iron Oxide | 6.0 |
| Propylene Carbonate | 1.0 |
| PureSyn ™ 2 | 2.0 |
| Silica Shells | 2.0 |
| Total | 100.0 |

In the main kettle, isododecane was heated to 65-80° C. Under mixing, REGALITE® R1100 was added and dissolved for (about 15 minutes). After the solid was completely dissolved, KRATON G 1657 M was added under vigorous mixing. The temperature was maintained between 60 and 80° C. After all solids were dissolved, the Uniclear was added and dissolved. After Uniclear was completely dissolved, black iron oxide was added using a homogenizer. While mixing for 1 hour keeping the temperature between 50-55° C. Still under the homogenizer, disteardimonium hectorite was added, and after 15-30 minutes propylene carbonate was added. The temperature was maintained at 50-55° C. After 30 minutes, heat was removed followed by cooling. Puresyn™ 2 was added and mixed well. Silica shells were added. Once uniformity was achieved, the mixture was transferred to a paddle mixer. When the temperature reached 30-35° C., the batch was dropped.

Example 4

| MATERIALS | AMOUNT |
|---|---|
| Isododecane | 56.00 |
| Regalite ® R 1100 | 16.00 |
| Kraton ™ G 1657 M | 2.00 |
| Uniclear 100 VG | 12.00 |
| Bentone | 3.00 |
| Black Iron Oxide | 6.00 |

-continued

| MATERIALS | AMOUNT |
|---|---|
| Propylene Carbonate | 1.00 |
| PureSyn ™ 2 | 2.00 |
| Silica Shells | 2.00 |
| TOTAL | 100.00 |

To make the mascara, isododecane was heated in the main kettle to a temperature of 65-80° C. Under mixing, Regalite® R 1100 was added and dissolved (about 15 minutes). After the solid was completely dissolved, the Kraton G 1657 M was added under vigorous mixing. The temperature was maintained between 60 and 80° C. After all solids were dissolved, the Uniclear 100 was added, and once that was dissolved, Black iron oxide was added while homogenizing. Mixing was continued for one hour while maintaining the temperature between 50-55° C. Bentone was added, and 15 minutes later, propylene carbonate was added, each under mixing and while maintaining the temperature between 50-55° C. Thirty minutes later, heating was stopped, followed by cooling, at which time, Puresyn™ 2 was added while mixing. Silica shells were then added. Once a uniform composition was achieved, it was transferred to a paddle mixer. When the temperature reached 30-35° C., the batch was dropped.

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A mascara composition, comprising a thermoplastic elastomer, a tackifier comprising a hydrogenated styrene/methyl styrene/indene copolymer, a volatile solvent and a non-polar non-volatile solvent.

2. The mascara composition of claim 1, wherein said thermoplastic elastomer has a thermoplastic segment comprising styrene.

3. The mascara composition of claim 2, wherein styrene comprises less than about 25% of the weight of said thermoplastic elastomer.

4. The mascara composition of claim 2, wherein styrene comprises less than about 13% of the weight of said thermoplastic elastomer.

5. The mascara composition of claim 1, wherein said thermoplastic elastomer comprises a styrene ethylene/butylene tri-block copolymer.

6. The mascara composition of claim 1, wherein said volatile solvent comprises a non-polar volatile solvent.

7. The mascara composition of claim 6, wherein said non-polar volatile solvent is isododecane.

8. The mascara composition of claim 6, wherein said non-polar volatile solvent comprises petroleum distillate.

9. The mascara composition of claim 1, wherein said non-volatile solvent comprises a polyalphaolefin.

10. The mascara composition of claim 9, wherein said polyalphaolefin comprises a polydecene.

11. The mascara composition of claim 10, wherein said polydecene is a hydrogenated polydecene.

12. The mascara composition of claim 11, wherein said polydecene has a molecular weight of about 283.

13. The mascara composition of claim 1, wherein said thermoplastic resin comprises a styrene ethylene/butylene tri-block copolymer and said non-volatile solvent comprises a polydecene.

14. The mascara composition of claim 1, further comprising water and an emulsifier.

15. The mascara composition of claim 14, wherein said emulsifier comprises a phosphate or an alkyl phosphate, and wherein said emulsifier does not contain triethanolamine.

16. The mascara composition of claim 15, wherein said emulsifier comprises potassium cetyl phosphate.

17. The mascara composition of claim 14, further comprising at least one wax.

18. The mascara composition of 14, further comprising a thickener.

19. The mascara composition of claim 18, wherein said thickener comprises PEG-100 Stearyl Ether/Dimer/IPDI.

20. A method of making mascara, comprising mixing together, a thermoplastic elastomer, a tackifier comprising a hydrogenated styrene/methyl styrene/indene copolymer, a volatile solvent, and a non-volatile solvent.

21. A method of applying make-up to eyelashes, comprising applying to the lashes a mascara composition comprising a thermoplastic elastomer, a tackifier comprising a hydrogenated styrene/methyl styrene/indene copolymer, a volatile solvent, and a non-volatile solvent.

22. The composition of claim 1, wherein the thermoplastic elastomer further comprises a styrene-ethylenebutylene diblock copolymer and a styrene ethylene/butylene tri-block copolymer.

23. The method of claim 20, wherein the thermoplastic elastomer further comprises a styrene-ethylenebutylene diblock copolymer and a styrene ethylene/butylene tri-block copolymer.

24. The method of claim 21, wherein the thermoplastic elastomer further comprises a styrene-ethylenebutylene diblock copolymer and a styrene ethylene/butylene tri-block copolymer.

* * * * *